US008532261B2

(12) United States Patent
Kamiya et al.

(10) Patent No.: US 8,532,261 B2
(45) Date of Patent: Sep. 10, 2013

(54) PORTABLE RADIOGRAPHIC APPARATUS SYSTEM

(75) Inventors: Takeshi Kamiya, Kanagawa (JP); Yusuke Kitagawa, Kanagawa (JP); Yasunori Ohta, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 335 days.

(21) Appl. No.: 13/067,361

(22) Filed: May 26, 2011

(65) Prior Publication Data

US 2011/0293070 A1 Dec. 1, 2011

(30) Foreign Application Priority Data

May 27, 2010 (JP) ................................ 2010-121966

(51) Int. Cl.
*H05G 1/10* (2006.01)
(52) U.S. Cl.
USPC .......................................................... 378/102
(58) Field of Classification Search
USPC ................................................. 378/102, 210
See application file for complete search history.

(56) References Cited

U.S. PATENT DOCUMENTS 5,729,587 A * 3/1998 Betz .............................. 378/198
7,916,834 B2 * 3/2011 Piorek et al. ................... 378/44

FOREIGN PATENT DOCUMENTS

JP 2001-224579 8/2001

* cited by examiner

*Primary Examiner* — Jurie Yun
(74) *Attorney, Agent, or Firm* — Jean C. Edwards, Esq.; Edwards Neils PLLC

(57) ABSTRACT

A portable radiographic apparatus system reduces the number of types of spare rechargeable battery. A first rechargeable battery for operation of a portable radiographic apparatus has the same shape and characteristics as a second rechargeable battery for operation of a portable X-ray source. The first rechargeable battery and the second rechargeable battery are interchangeable. When, in order capture images during a visit to an individual's home or a visit to a nursing facility, the portable radiographic apparatus and the portable X-ray source are taken to the visit destination, spare rechargeable batteries must be taken in case of trouble with the rechargeable batteries. Because the first rechargeable battery and the second rechargeable battery are interchangeable, by bringing either the first rechargeable battery or the second rechargeable battery, trouble can be addressed if it arises. In this way, the number of types of spare rechargeable battery can be reduced.

6 Claims, 11 Drawing Sheets

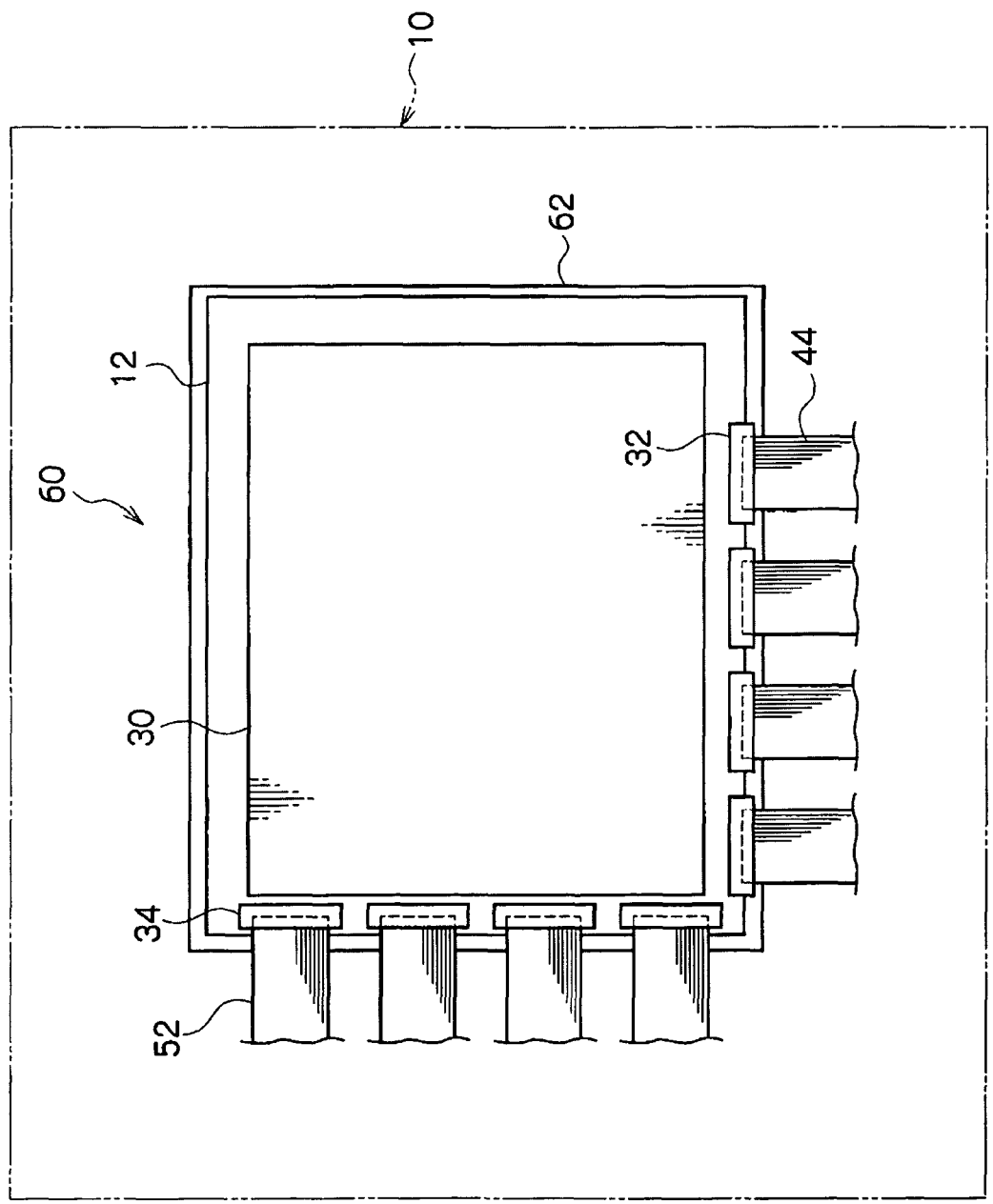

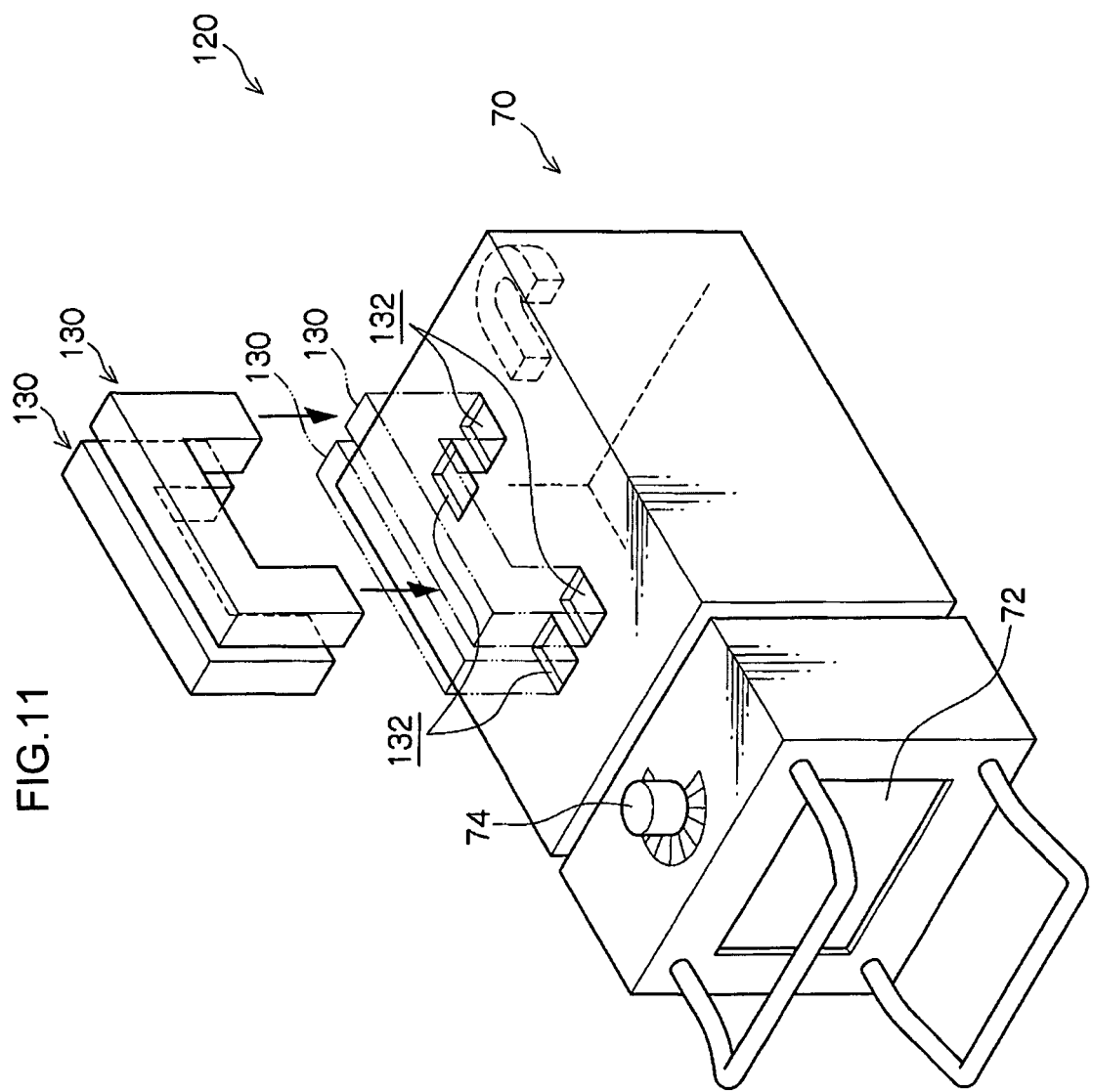

PORTABLE RADIOGRAPHIC APPARATUS SYSTEM

CROSS-REFERENCE TO RELATED APPLICATION

This application claims priority under 35 USC 119 from Japanese Patent Application No. 2010-121966 filed on May 27, 2010, the disclosure of which is incorporated by reference herein.

BACKGROUND

1. Technical Field

The present invention relates to a portable radiographic apparatus system that is equipped with a portable radiographic apparatus and a portable X-ray source.

2. Related Art

Japanese Patent Application Laid-Open (JP-A) No. 2001-224579 discloses a portable radiographic apparatus (an X-ray detector). This portable radiographic apparatus operates by electric power from a rechargeable battery that is provided so as to be freely installed in and removed from the portable radiographic apparatus.

However, the conventional art does not disclose means for supplying electric power to a portable X-ray source that irradiates radiation toward the portable radiographic apparatus. Even if the portable X-ray source as well is structured so as to be operated by a rechargeable battery, there are cases in which the portable radiographic apparatus and the portable X-ray source are brought and used in a visit to an individual's home or a visit to a nursing facility or the like. In such cases, in consideration of trouble with the rechargeable batteries, two types of spare rechargeable batteries, that are a spare rechargeable battery for the portable radiographic apparatus and a spare rechargeable battery for operating the portable X-ray source, must be readied.

SUMMARY

An object of the present invention is to reduce the number of types of spare rechargeable batteries.

A portable radiographic apparatus system of a first aspect of the present invention comprises: a portable radiographic apparatus that is operated by electric power supplied thereto from a first rechargeable battery, and that records radiographic images expressed by irradiated radiation; and a portable X-ray source that is operated by electric power supplied thereto from a second rechargeable battery that has a same shape and same characteristics as the first rechargeable battery, and that irradiates radiation toward the portable radiographic apparatus.

In accordance with the above-described structure, the portable radiographic apparatus, to which electric power is supplied from the first rechargeable battery, records radiographic images that are expressed by irradiated radiation. Further, the portable X-ray source, to which electric power is supplied from the second rechargeable battery that has the same shape and same characteristics as the first rechargeable battery, irradiates radiation toward the portable radiographic apparatus. Here, because the first rechargeable battery and the second rechargeable battery have the same shape and the same characteristics, they are interchangeable.

For example, when, in order to capture images during a visit to an individual's home or a visit to a nursing facility, the portable radiographic apparatus and the portable X-ray source are brought to the destination of the visit, spare rechargeable batteries must be brought along in consideration of trouble with the rechargeable batteries.

As described above, the first rechargeable battery and the second rechargeable battery are interchangeable. Therefore, by bringing either one of the first rechargeable battery or the second rechargeable battery as a spare, trouble can be addressed when it arises. By making the first rechargeable battery and the second rechargeable battery be interchangeable in this way, the number of types of spare rechargeable batteries can be reduced.

A portable radiographic apparatus system of a second aspect of the present invention is the portable radiographic apparatus system of the first aspect of the present invention, wherein a first attachment portion, to which the first rechargeable battery is attached so as to be freely attachable thereto and detachable therefrom, is provided at the portable radiographic apparatus, a second attachment portion, to which the second rechargeable battery is attached so as to be freely attachable thereto and detachable therefrom, is provided at the portable X-ray source, and a total number of the first attachment portions and a total number of the second attachment portions is determined on the basis of consumed electric power of the portable radiographic apparatus and the portable X-ray source per unit number of images at a time of recording radiographic images.

In accordance with the above-described structure, the total number of the first attachment portions, to which the first rechargeable battery is attached so as to be freely attachable thereto and detachable therefrom, and the total number of the second attachment portions, to which the second rechargeable battery is attached so as to be freely attachable thereto and detachable therefrom, are determined on the basis of the consumed electric powers of the portable radiographic apparatus and the portable X-ray source per unit number of images at a time of recording the radiographic images.

Due thereto, the rates of consumption of the charged amounts of the first rechargeable battery and the second rechargeable battery at the time of capturing images are substantially the same, and the electric powers of the first rechargeable battery and the second rechargeable battery can be consumed without waste.

A portable radiographic apparatus system of a third aspect of the present invention is the portable radiographic apparatus system of the first aspect or the second aspect of the present invention, wherein in a state of being attached to the first attachment portion and the second attachment portion, the first rechargeable battery and the second rechargeable battery function as handles of the portable radiographic apparatus and the portable X-ray source, respectively.

In accordance with the above-described structure, in a state of being attached to the first attachment portion and the second attachment portion, the first rechargeable battery and the second rechargeable battery become handles of the portable radiographic apparatus and the portable X-ray source.

Due thereto, when the portable radiographic apparatus and the portable X-ray source are to be carried, the first rechargeable battery and the second rechargeable battery that are attached to the first attachment portion and the second attachment portion are grasped, and the portable radiographic apparatus and the portable X-ray source can be carried.

A portable radiographic apparatus system of a fourth aspect of the present invention is the portable radiographic apparatus system of the first aspect of the present invention, wherein an accommodating unit is provided that accommodates at least one of the first rechargeable battery or the second rechargeable battery, and that has an electric cable that supplies electric power from the first rechargeable battery or the second rechargeable battery to the portable radiographic apparatus or the portable X-ray source.

In accordance with the above-described structure, the portable radiographic apparatus or the portable X-ray source is connected to the accommodating unit via the electric cable. Due thereto, the portable radiographic apparatus or the portable X-ray source operates due to the electric power of the first rechargeable battery or the second rechargeable battery, that is accommodated in the accommodating unit, being supplied thereto.

In this way, the portable radiographic apparatus and the portable X-ray source can be operated by being supplied with electric power from the same rechargeable battery (the first rechargeable battery or the second rechargeable battery).

A portable radiographic apparatus system of a fifth aspect of the present invention is the portable radiographic apparatus system of the forth aspect of the present invention, wherein a charging cable, that can charge the first rechargeable battery or the second rechargeable battery accommodated in the accommodating unit with electric power from an exterior, is provided at the accommodating unit.

In accordance with the above-described structure, the first rechargeable battery or the second rechargeable battery that is accommodated in the accommodating unit is charged by connecting the charging cable, that is provided at the accommodating unit, to an outlet for example.

In this way, the first rechargeable battery and the second rechargeable battery can be charged by a simple method.

In accordance with the present invention, the number of types of spare rechargeable batteries can be reduced.

BRIEF DESCRIPTION OF THE DRAWINGS

Exemplary embodiments of the present invention will be described in detail based on the following figures wherein:

FIG. 7 is a plan view showing the portable radiographic apparatus that is provided at the portable radiographic apparatus system relating to the first exemplary embodiment of the present invention;

FIG. 11 is a perspective view showing a portable X-ray source that is provided at the portable radiographic apparatus system relating to the third exemplary embodiment of the present invention.

DETAILED DESCRIPTION

Figure 1A:
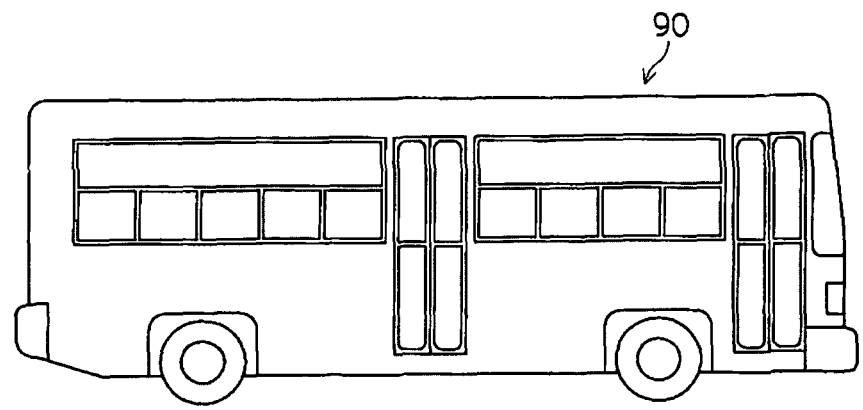
FIG. 1A is a structural drawing showing a portable radiographic apparatus and a portable X-ray source that are provided at a portable radiographic apparatus system relating to a first exemplary embodiment of the present invention.

An example of a portable radiographic apparatus system 64 relating to a first exemplary embodiment of the present invention is described in accordance with FIG. 1A, FIG. 1B through FIG. 7. Note that arrow UP in the drawings indicates upward in the vertical direction.

(Overall Structure)

Figure 1B:
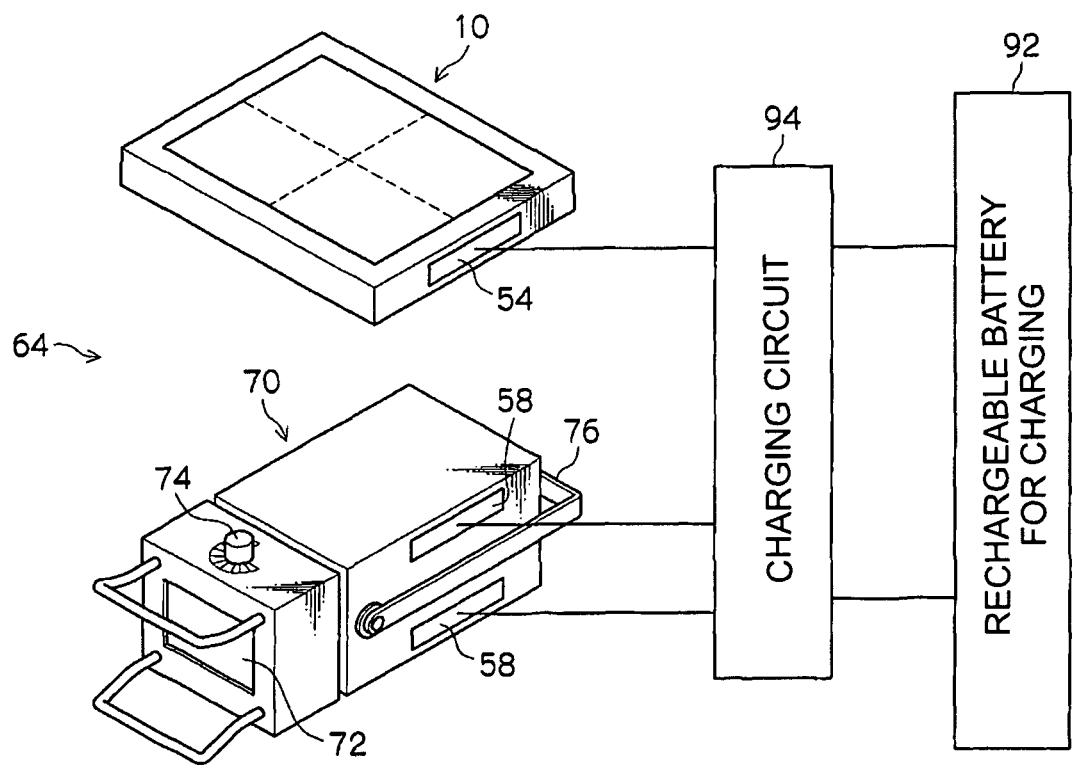
FIG. 1B is a structural drawing showing the portable radiographic apparatus and the portable X-ray source that are provided at the portable radiographic apparatus system relating to the first exemplary embodiment of the present invention.
Figure 5:
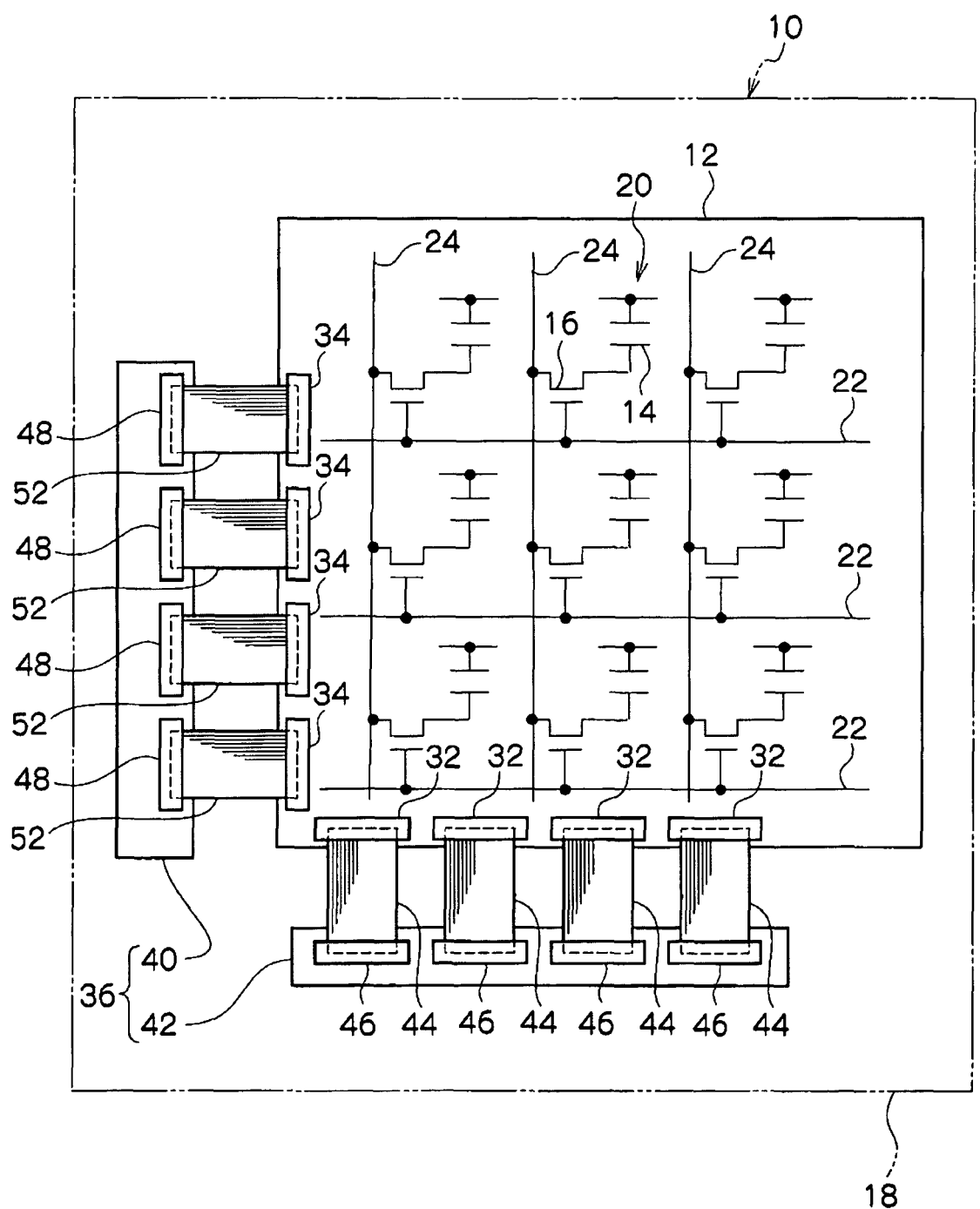
FIG. 5 is a circuit diagram showing the portable radiographic apparatus that is provided at the portable radiographic apparatus system relating to the first exemplary embodiment of the present invention.

As shown in FIG. 5, a radiographic element 12 is provided within a housing 18 of a portable radiographic apparatus 10 (a so-called electronic cassette) that is provided at the portable radiographic apparatus system 64 (see FIG. 1B). The radiographic element 12 has an upper electrode, a semiconductor layer, and a lower electrode. Numerous pixels 20, that are structured to include a sensor portion 14 that receives light and accumulates charges and a TFT switch 16 for reading-out the charges accumulated in the sensor portion 14, are provided in a two-dimensional form at the radiographic imaging element 12.

Plural scan lines 22, for turning the TFT switches 16 on and off, and plural signal lines 24, for reading-out the charges accumulated in the sensor portions 14, are provided at the radiographic element 12 so as to intersect one another.

A scintillator 30 (see FIG. 6 and FIG. 7) formed from GOS or CsI or the like is adhered to the surface of the radiographic element 12 relating to the present exemplary embodiment. In order to prevent generated light from leaking-out to the exterior, the scintillator 30 has a light-blocking body 30A (see FIG. 6) that blocks the generated light, at the surface at the side opposite the adhered radiographic element 12.

At the radiographic element 12, radiation such as X-rays or the like that is irradiated is converted into light at the scintillator 30, and the light is illuminated onto the sensor portions 14. The sensor portions 14 receive the light illuminated from the scintillator 30, and accumulate charges.

Further, due to any of the TFT switches 16 connected to the signal line 24 being turned on, an electric signal (image signal), that expresses a radiographic image in accordance with the charge amount accumulated in the sensor portion 14, flows to the signal line 24.

Plural connectors 32 for connection are provided so as to be lined-up at one end side, in the signal line direction, of the radiographic element 12. Plural connectors 34 are provided so as to be lined-up at one end side in the scan line direction.

The respective signal lines 24 are connected to the connectors 32, and the respective scan lines 22 are connected to the connectors 34.

Further, a control section 36, that carries out control of radiation detection by the radiographic element 12 and control of signal processing with respect to the electric signals flowing to the respective signal lines 24, is provided in the present exemplary embodiment. The control section 36 has a signal detection circuit 42 and a scan signal control circuit 40.

Plural connectors 46 are provided at the signal detection circuit 42. Ones of ends of flexible cables 44 are electrically connected to the connectors 46. The other ends of the flexible cables 44 are connected to the connectors 32, and an amplifying circuit that amplifies the inputted electric signal is incorporated for each of the signal lines 24. In accordance with this structure, due to the electric signals inputted from the respective signal lines 24 being amplified by the amplification circuits and detected, the signal detection circuit 42 detects the charge amounts accumulated in the respective sensor portions 14, as information of the respective pixels 20 that structure the image.

On the other hand, connectors 48 are provided at the scan signal control circuit 40, and ones of ends of flexible cables 52 are electrically connected to the connectors 48. The other ends of the flexible cables 52 are connected to the connectors 34. The scan signal control circuit 40 outputs, to the respective scan lines 22, control signals for turning the TFT switches 16 on and off.

Figure 6:
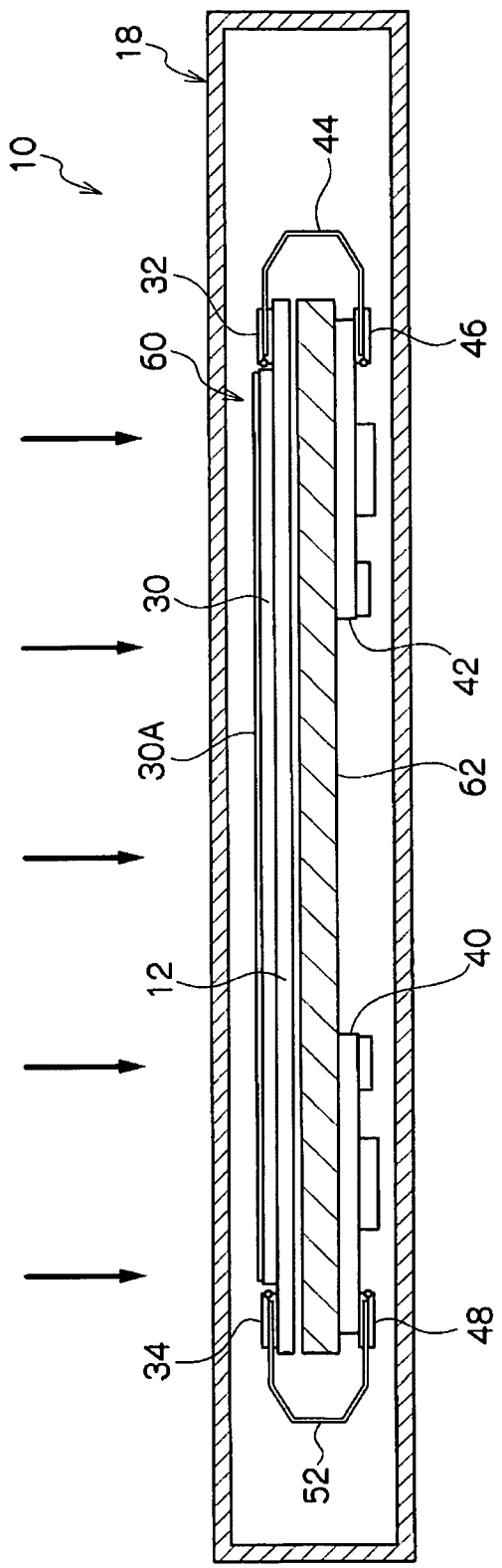
FIG. 6 is a cross-sectional view showing the portable radiographic apparatus that is provided at the portable radiographic apparatus system relating to the first exemplary embodiment of the present invention.

Further, as shown in FIG. 6, the portable radiographic apparatus 10 relating to the present exemplary embodiment has an imaging section 60 that captures the radiographic image expressed by the radiation that was irradiated. At the imaging section 60, the radiographic element 12 is disposed at one surface of a supporting substrate 62 that is formed in the shape of a flat plate (see FIG. 5), and the signal detection circuit 42 and the scan signal control circuit 40, that correspond to the radiographic element 12, are disposed at the other surface of the supporting substrate 62.

Figure 3:
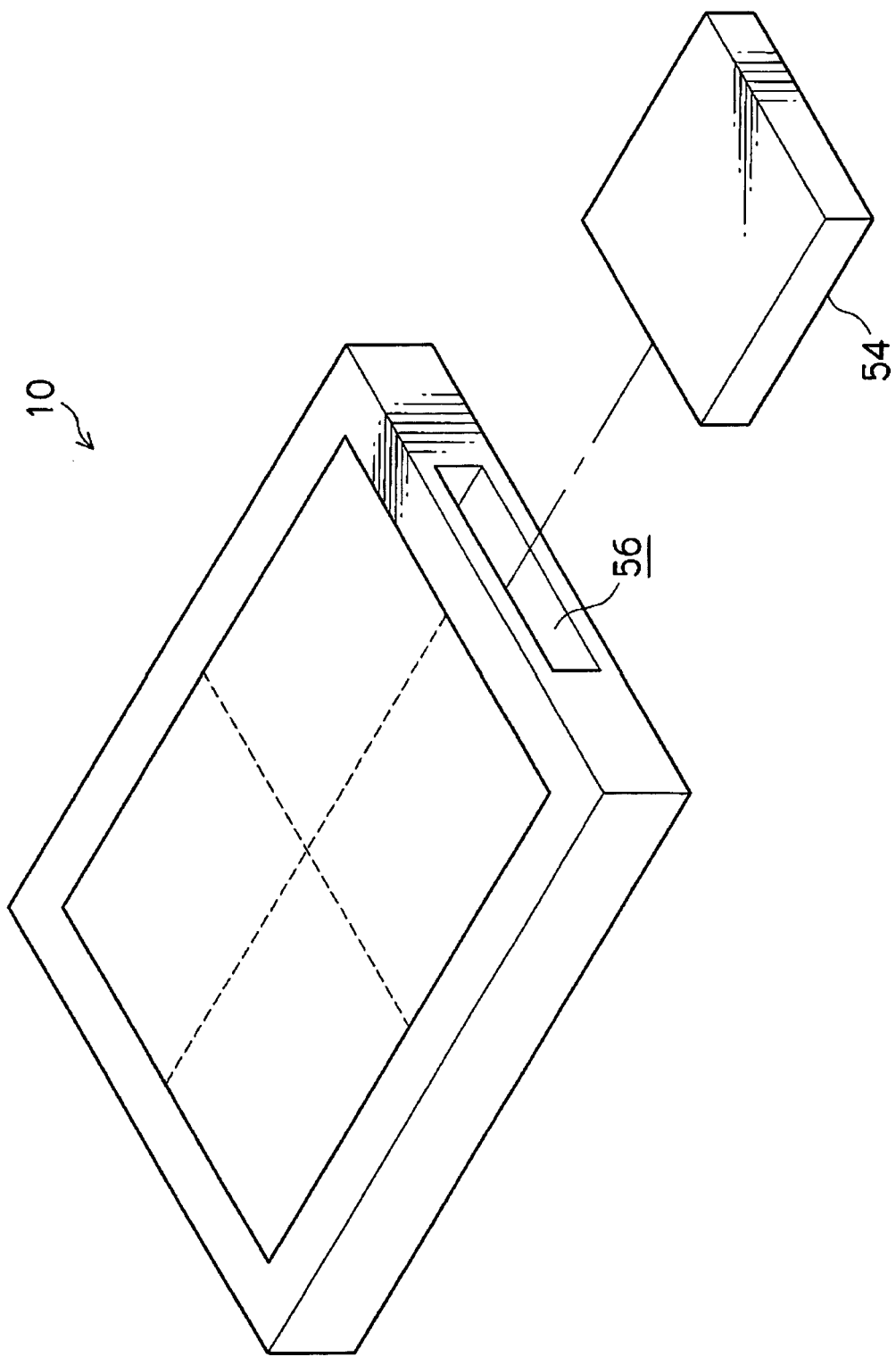
FIG. 3 is a perspective view showing the portable radiographic apparatus that is provided at the portable radiographic apparatus system relating to the first exemplary embodiment of the present invention.

Further, as shown in FIG. 3, a rechargeable battery 54 for operation, that serves as a first rechargeable battery and causes the portable radiographic apparatus 10 to work, is provided at the portable radiographic apparatus 10. The rechargeable battery 54 for operation can be freely installed in and removed from an accommodating portion 56 that serves as a first attachment portion and is provided in a side surface of the portable radiographic apparatus 10.

Figure 4:
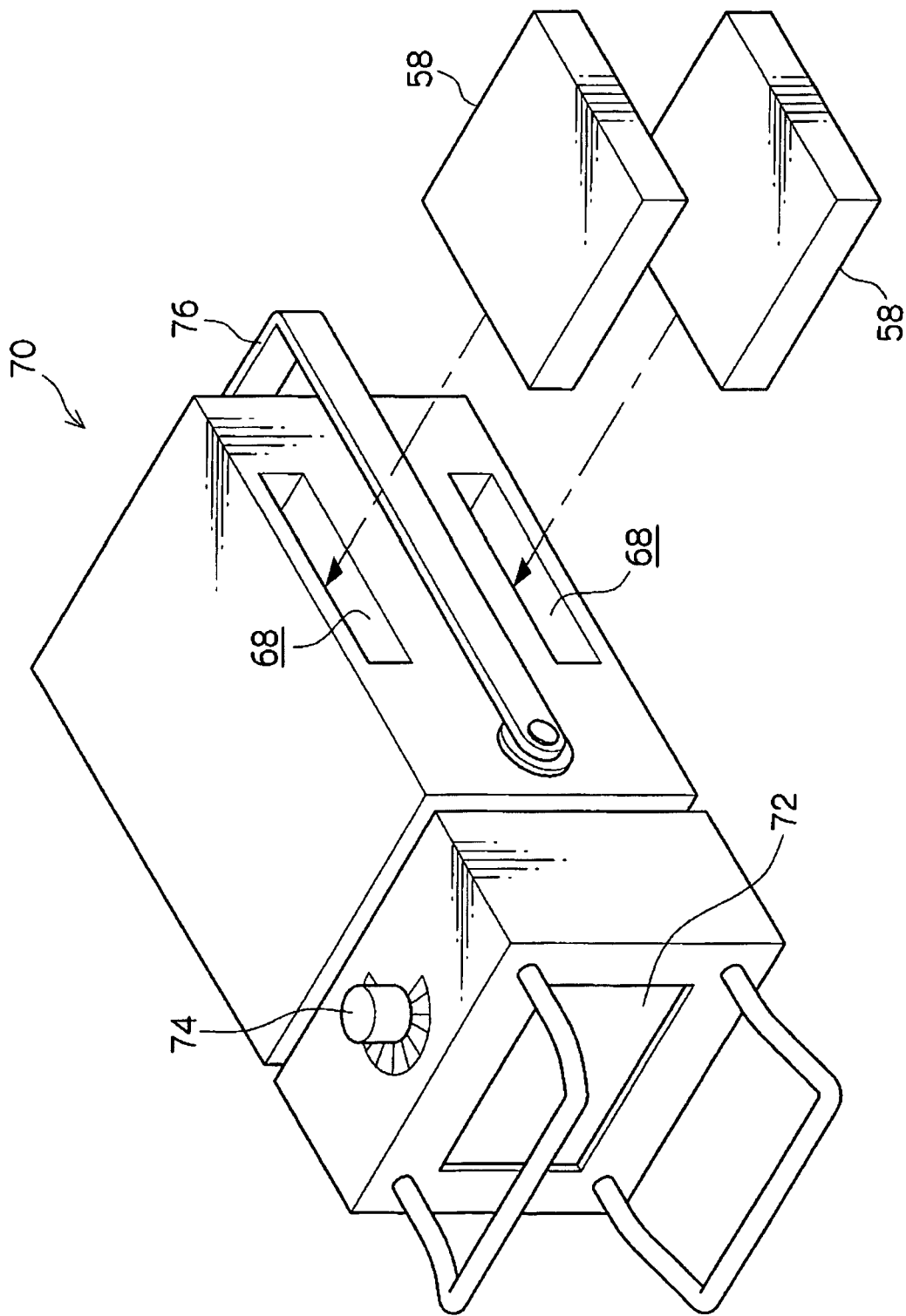
FIG. 4 is a perspective view showing the portable X-ray source that is provided at the portable radiographic apparatus system relating to the first exemplary embodiment of the present invention.

In contrast, as shown in FIG. 4, at a portable X-ray source 70 that irradiates radiation toward the portable radiographic apparatus 10, there are provided an irradiation window 72 through which X-rays are irradiated, an adjustment dial 74 that adjusts the collimator of the portable X-ray source 70, and a handle portion 76 that is grasped when carrying the portable X-ray source 70.

Further, two rechargeable batteries 58 for operation, that serve as second rechargeable batteries and make the portable X-ray source 70 operate, are provided at the portable X-ray source 70. Two accommodating portions 68, that serve as second attachment portions and accommodate the rechargeable batteries 58 for operation, are provided in a side surface of the portable X-ray source 70. The rechargeable batteries 58 for operation are freely installed in and removed from the accommodating portions 68. Note that the rechargeable batteries 54, 58 for operation, and the method of charging the rechargeable batteries 54, 58 for operation, are described in detail later.

Operation of the portable radiographic apparatus 10 and the portable X-ray source 70 relating to the present exemplary embodiment is described next.

Figure 2:
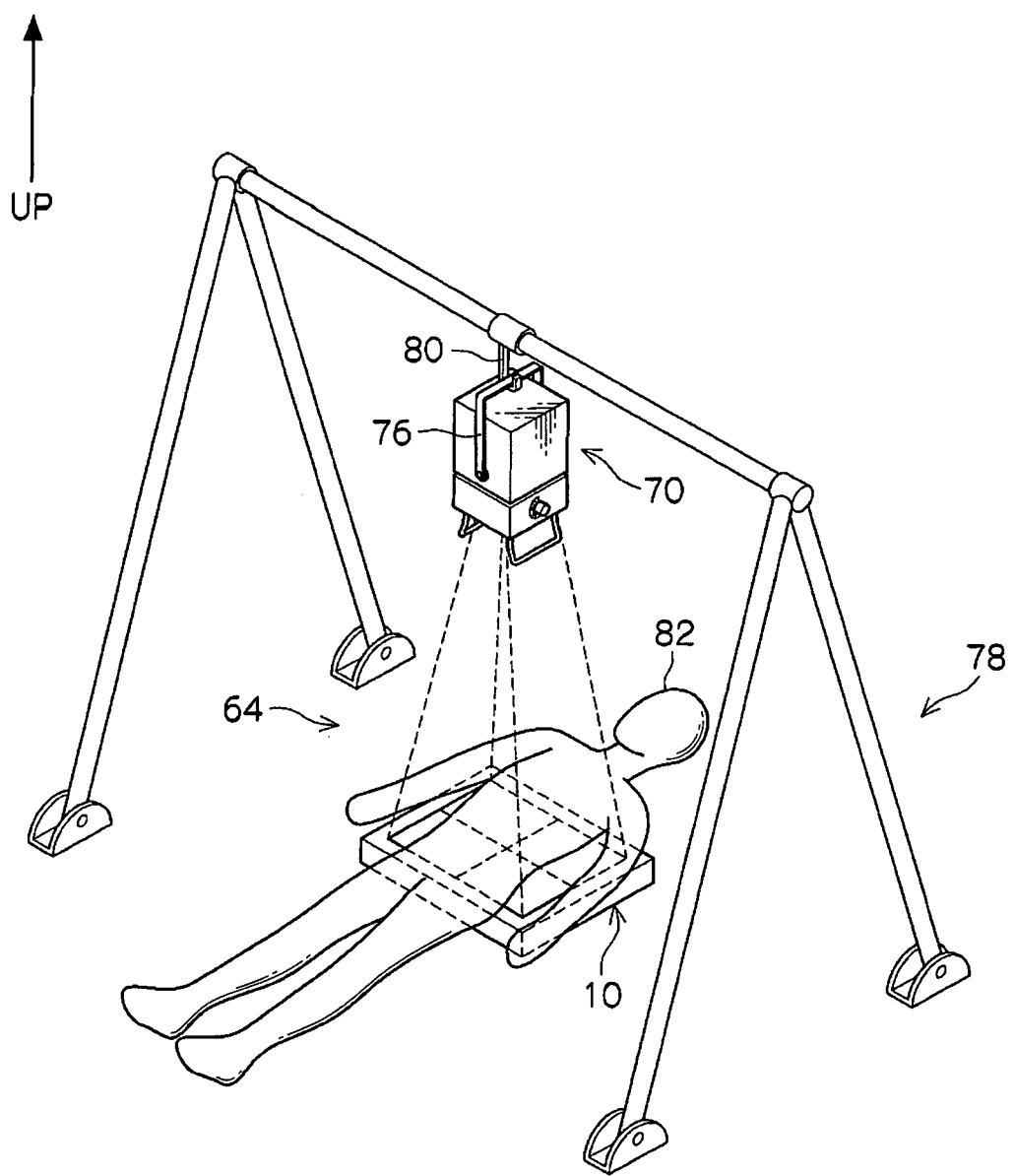
FIG. 2 is a perspective view showing the portable radiographic apparatus system relating to the first exemplary embodiment of the present invention.

As shown in FIG. 2, the portable radiographic apparatus 10 and the portable X-ray source 70 are placed in an automobile 90 (see FIG. 1A) that will be described later, and are carried to the home of an individual or to a nursing facility. Then, at the time of capturing radiographic images, the portable radiographic apparatus 10 is disposed with an interval between the portable radiographic apparatus 10 and the portable X-ray source 70 that generates radiation. In detail, the portable radiographic apparatus 10 and the portable X-ray source 70 are disposed with an interval in the vertical direction therebetween, by hooking the handle portion 76 of the portable X-ray source 70 on a hook portion 80 of a frame 78 that is easily assembled at the individual's home or nursing facility.

Further, the region between the portable X-ray source 70 and the portable radiographic apparatus 10 at this time is an imaging position for the positioning of a subject 82. When capturing of a radiographic image is instructed, the portable X-ray source 70 emits radiation of a radiation amount corresponding to imaging conditions and the like that are given in advance. Then, due to the radiation, that is emitted from the portable X-ray source 70, passing through the subject 82 positioned at the imaging position, the radiation carries image information, and thereafter, is irradiated onto the portable radiographic apparatus 10.

As shown in FIG. 6, at the radiographic imaging element 12, the radiation such as X-rays or the like that has been irradiated is converted into light at the scintillator 30, and the light is illuminated onto the sensor portions 14 (see FIG. 5). The sensor portions 14 receive the light illuminated from the scintillator 30, and accumulate charges.

As shown in FIG. 5, at the time of image read-out, on signals (+10 to 20 V) are successively applied from the scan signal control circuit 40 via the scan lines 22 to gate electrodes of the TFT switches 16 of the radiographic element 12. Due thereto, due to the TFT switches 16 of the radiographic element 12 successively being turned on, electric signals corresponding to the charge amounts accumulated in the sensor portions 14 flow-out to the signal lines 24. On the basis of the electric signals that have flowed-out to the signal lines 24 of the radiographic element 12, the signal detection circuit 42 detects the charge amounts accumulated in the respective sensor portions 14, as information of the respective pixels 20 structuring the image. Due thereto, image information, that expresses the image expressed by the radiation that was irradiated onto the radiographic element 12, is obtained.

(Main Portions)

The rechargeable batteries 54, 58 for operation, and the method of charging the rechargeable batteries 54, 58 for operation, are described next.

The rechargeable battery 54 for operation has the same shape and the same characteristics as the rechargeable battery 58 for operation, and the rechargeable battery 54 for operation and the rechargeable battery 58 for operation are interchangeable.

Further, as described above, the one accommodating portion 56 that accommodates the rechargeable battery 54 for operation is provided at the portable radiographic apparatus 10 as shown in FIG. 3. In contrast, as shown in FIG. 4, the two accommodating portions 68 that accommodate the rechargeable batteries 58 for operation are provided in the portable X-ray source 70.

Here, the numbers of the accommodating portions 56 and the accommodating portions 68 are determined on the basis of the electric power that is consumed per unit number of images at the time of recording radiographic images. In detail, at the time of designing the portable radiographic apparatus 10 and the portable X-ray source 70, the electric power that is consumed per unit number of images at the time of recording radiographic images is measured with respect to each of the portable radiographic apparatus 10 and the portable X-ray source 70, and the numbers of the accommodating portions 56, 68 are determined so as to conform to the following expression, and the accommodating portions 56, 68 are provided. Note that the electric power consumed per unit number of images is the electric power that is consumed per a predetermined number of images (e.g., one image), and is the electric power that is consumed at the time of recording that number of images.

(electric power consumed per unit number of images of the portable radiographic apparatus 10)/(electric power consumed per unit number of images of the portable X-ray source 70)=(number of accommodating portions 56)/(number of accommodating portions 68)

Note that, in consideration of individual differences in the electric powers consumed per unit number of images of the portable radiographic apparatus 10 and the portable X-ray source 70, the consumed electric powers of plural individual devices are measured, and a representative value is appropriately selected from the plural measured values. For example, the consumed electric power that is made to be the representative value can be selected appropriately from the following values.

1. a value in which a margin (around 10%) is added to the maximum consumed electric power (this value is thought to be the best from the standpoint of preventing the rechargeable battery for operation from running out of power)
2. the value of the maximum electric power consumed
3. σ (where σ is the standard deviation)
4. the average value
5. the mode value On the other hand, as shown in FIG. 1A and FIG. 1B, a rechargeable battery 92 for charging, that charges the rechargeable batteries 54, 58 for operation, is provided. This rechargeable battery 92 for charging is installed in the automobile 90. The automobile 90 is a gasoline-powered vehicle that runs by using gasoline as fuel. The rechargeable battery 92 for charging is the electric power source that supplies electric power to the electrical parts (e.g., the headlights) of the automobile 90.

In detail, a charging circuit 94, that can charge the rechargeable batteries 54, 58 for operation by the rechargeable battery 92 for charging, is provided in the automobile 90. Then, when the portable radiographic apparatus 10 and the portable X-ray source 70 are to be used during a visit to an individual's home or a visit to a nursing facility or the like for example, the rechargeable batteries 54, 58 for operation are charged by the rechargeable battery 92 for charging via the charging circuit 94, in the automobile 90 that is moving.

Further, the capacity of the rechargeable battery 92 for charging is greater than the capacity of the rechargeable batteries 54, 58 for operation. Moreover, the self-discharge rate of the rechargeable battery 92 for charging is small as compared with the rechargeable batteries 54, 58 for operation. Namely, it is difficult for the rechargeable battery 92 for charging to discharge, as compared with the rechargeable batteries 54, 58 for operation.

The method of calculating and the method of measuring the self-discharge rate are described below.

self-discharge rate[%] of battery=(initial discharge capacity−discharge capacity after storage)/initial discharge capacity×100

<Measuring Method>

First Step: A single battery or a battery pack is charged at an ambient temperature of 20±5° C. by a method specified by the manufacturer.

Second Step: The single battery or battery pack is discharged, at an ambient temperature of 20±5° C., at a constant current of $0.2I_t$ [A] until the battery voltage becomes a prescribed discharge end voltage. The discharge amount at this time is the initial discharge capacity. Here, $I_t$ [A] is the hourly-rate current of the single battery or the battery pack.

Third Step: The single battery or battery pack is charged at an ambient temperature of 20±5° C. by a method specified by the manufacturer.

Fourth Step: The single battery or battery pack is left for 28 days in an ambient temperature of 20±5° C.

Fifth Step: The single battery or battery pack is discharged, at an ambient temperature of 20±5° C., at a constant current of $0.2I_t$ [A] until the battery voltage becomes a prescribed discharge end voltage. The discharge amount at this time is the discharge capacity after storage.

(Operation/Effects)

The operation and effects of the portable radiographic apparatus system 64 are described next.

As shown in FIG. 1A and FIG. 1B, when, due to imaging being carried out during a visit to an individual's home or a visit to a nursing facility or the like, the portable radiographic apparatus 10 and the portable X-ray source 70 are to be brought to the destination of the visit and used thereat, the portable radiographic apparatus 10 and the portable X-ray source 70 are loaded into the automobile 90 for moving.

When the charged amount of the rechargeable battery 54, 58 for operation that is accommodated in the portable radiographic apparatus 10 or the portable X-ray source 70 loaded in the automobile 90 is low, or when there are several destinations to visit and the charged amount of the rechargeable battery 54, 58 has become low in the midst thereof, the rechargeable battery 54, 58 for operation is charged during moving by using the rechargeable battery 92 for charging that is installed in the automobile 90.

Here, when, in order to carry out imaging when visiting the home of an individual or visiting a nursing facility, the portable radiographic apparatus 10 and the portable X-ray source 70 are brought to the destination of the visit, spare rechargeable batteries must be brought along in consideration of trouble with the rechargeable batteries.

As mentioned above, the rechargeable battery 54 for operation and the rechargeable battery 58 for operation are interchangeable. Therefore, by bringing either one of the rechargeable battery 54 for operation or the rechargeable battery 58 for operation, trouble can be addressed when it arises. In this way, the number of types of spare rechargeable batteries can be reduced.

Further, the number of the accommodating portions 56 in which the rechargeable battery 54 for operation is accommodated, and the number of the accommodating portions 68 in which the rechargeable battery 58 for operation is accommodated, are determined on the basis of the consumed electric powers of the portable radiographic apparatus 10 and the portable X-ray source 70 per unit number of images at the time of recording radiographic images. Due thereto, the rates of consumption of the charged amounts of the rechargeable battery 54 for operation and the rechargeable battery 58 for operation at the time of capturing images are substantially the same, and the electric powers of the rechargeable battery 54 for operation and the rechargeable battery 58 for operation can be consumed without waste.

The rechargeable batteries 54, 58 for operation are freely installed in and removed from the portable radiographic apparatus 10 and the portable X-ray source 70. When trouble arises such as charging from the rechargeable battery 92 for charging cannot be carried out, the portable radiographic apparatus 10 and the portable X-ray source 70 can be made to operate by replacing the rechargeable batteries 54, 58 for operation, that are installed in the portable radiographic apparatus 10 and the portable X-ray source 70, with the spare rechargeable batteries 54, 58 for operation.

Note that, although the present invention has been described in detail with reference to a specific exemplary embodiment, the present invention is not limited to this embodiment, and it will be clear to those skilled in the art that various other embodiments are possible within the scope of the present invention. For example, although not described in particular in the above exemplary embodiment, a personal computer, such as a notebook type or the like, that controls the portable radiographic apparatus 10 and the portable X-ray source 70 may be used when images of the subject 82 are captured by using the portable radiographic apparatus 10 and the portable X-ray source 70. Further, this personal computer may be made to operate by the rechargeable batteries 54, 58 for operation.

Moreover, the above exemplary embodiment describes using the rechargeable battery 92 for charging that is used in the automobile 90 (a gasoline-powered vehicle) that runs by using gasoline as fuel. However, the present invention is not particularly limited to the same and may use, as the rechargeable battery for charging, a rechargeable battery that is used in a diesel-powered vehicle, a hybrid car, an electric vehicle, or the like.

An example of a portable radiographic apparatus system 100 relating to a second exemplary embodiment of the present invention is described next in accordance with FIG. 8A, FIG. 8B and FIG. 9. Note that members that are the same as in the first exemplary embodiment are denoted by the same reference numerals, and description thereof is omitted.

Figure 8A:
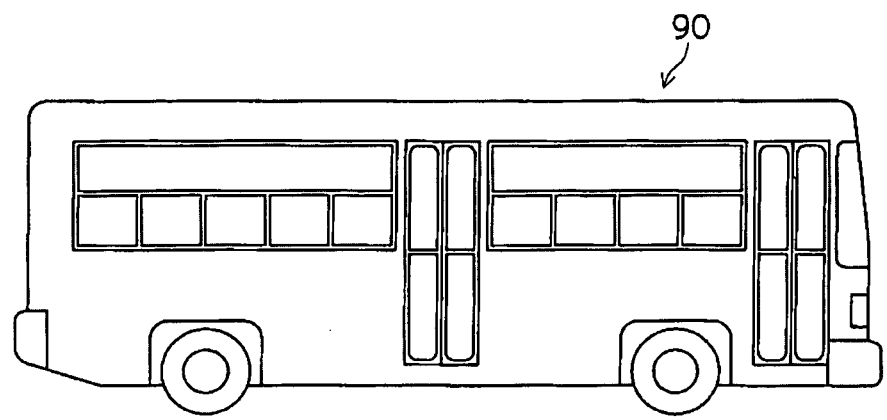
FIG. 8A is a structural drawing showing a portable radiographic apparatus and a portable X-ray source that are provided at a portable radiographic apparatus system relating to a second exemplary embodiment of the present invention.
Figure 8B:
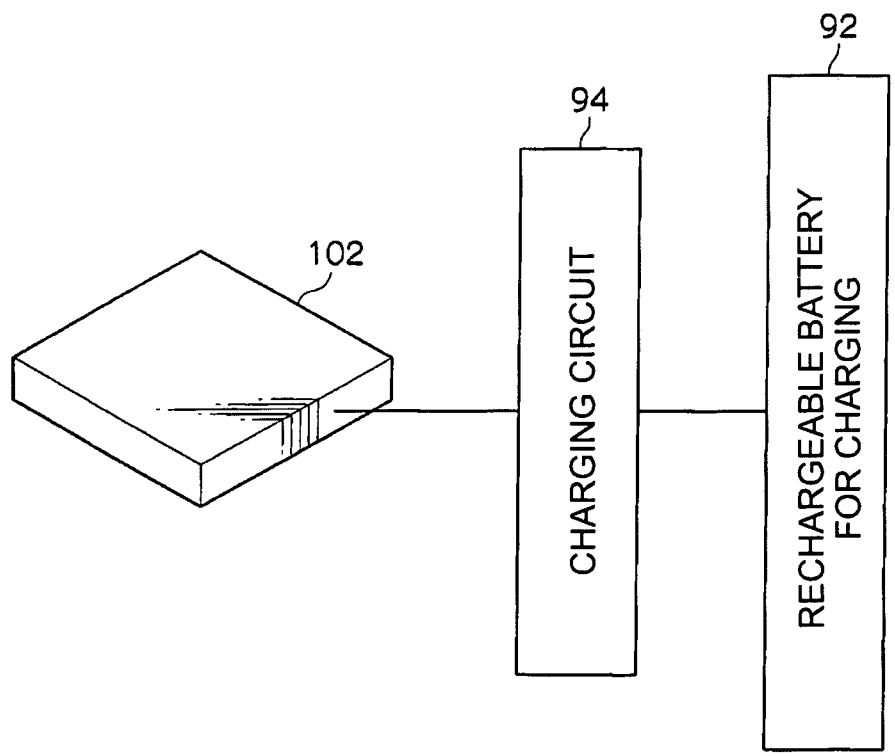
FIG. 8B is a structural drawing showing the portable radiographic apparatus and the portable X-ray source that are provided at the portable radiographic apparatus system relating to the second exemplary embodiment of the present invention.

As shown in FIG. 8A and FIG. 8B, a rechargeable battery 102 for operation, that makes the portable radiographic apparatus 10 and the portable X-ray source 70 operate, is directly charged from the rechargeable battery 92 for charging, via the charging circuit 94.

Figure 9:
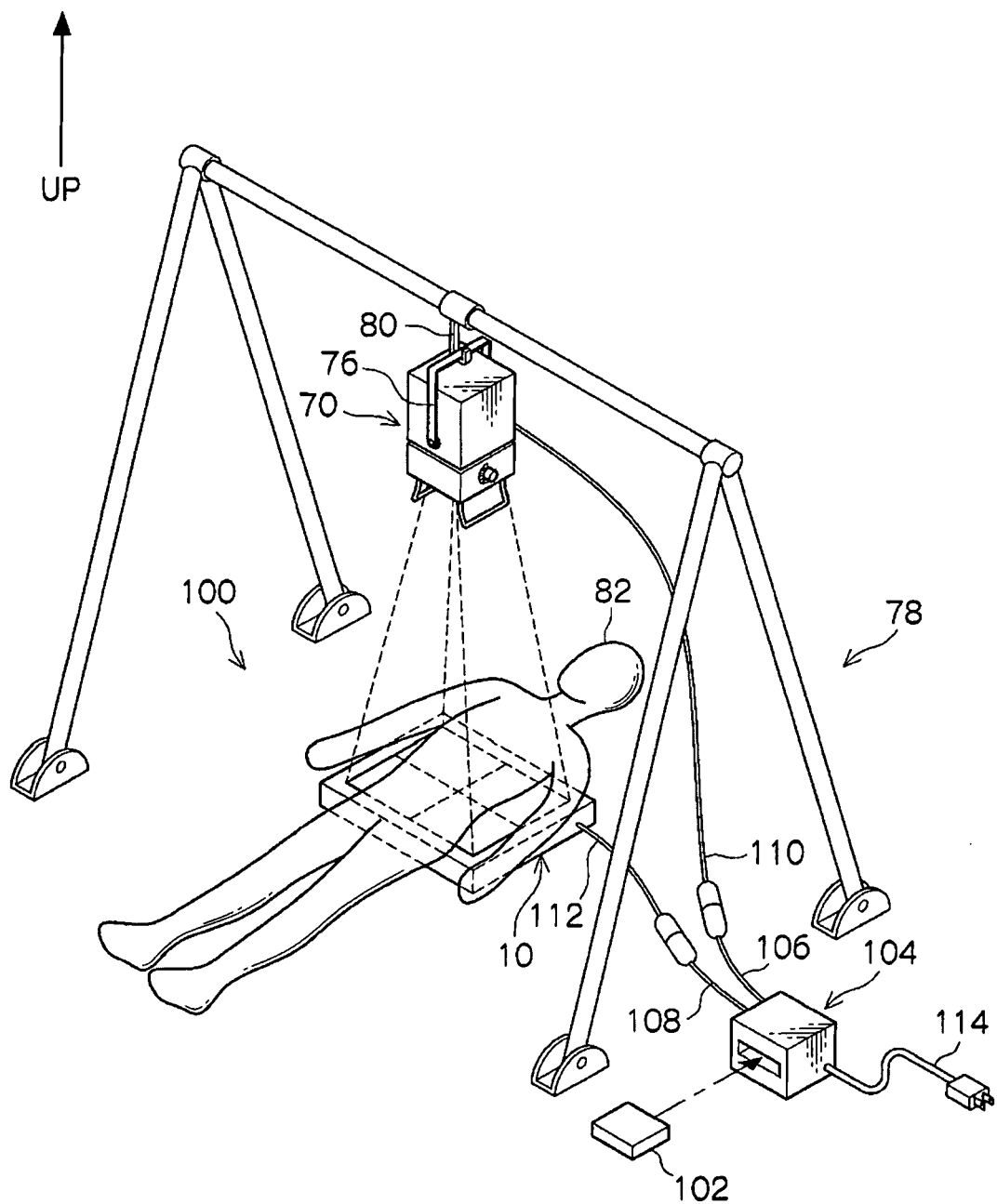
FIG. 9 is a perspective view showing the portable radiographic apparatus system relating to the second exemplary embodiment of the present invention.

Further, as shown in FIG. 9, an accommodating unit 104 that accommodates the rechargeable battery 102 for operation is provided. At the destination of a visit, when electric power is to be supplied to the portable radiographic apparatus 10 and the portable X-ray source 70, the rechargeable battery 102 for operation is accommodated in the accommodating unit 104. Moreover, electric cables 106, 108 provided at the accommodating unit 104 are connected to electric cables 110, 112 that extend from the portable radiographic apparatus 10 and the portable X-ray source 70. Due thereto, the rechargeable battery 102 for operation supplies electric power, via the accommodating unit 104, to the portable radiographic apparatus 10 and the portable X-ray source 70.

A power source cable 114 serving as a charging cable is provided at the accommodating unit 104. By connecting the power source cable 114 to an outlet (e.g., a wall outlet) that can supply electric power, the rechargeable battery 102 for operation that is accommodated in the accommodating unit 104 is charged via a charging circuit (not illustrated) provided in the accommodating unit 104.

Namely, the rechargeable battery 102 for operation can be charged from the rechargeable battery 92 for charging while traveling to the destination of a visit. At the destination of the visit, the rechargeable battery 102 for operation can be charged by being accommodated in the accommodating unit 104 and by the power source cable 114 being inserted into an outlet.

As described above, the portable radiographic apparatus 10 and the portable X-ray source 70 can be operated by electric power being supplied thereto from the same rechargeable battery (the rechargeable battery 102 for operation).

Further, the rechargeable battery 102 for operation that is accommodated in the accommodating unit 104 is charged by connecting the power source cable 114, that is provided at the accommodating unit 104, to an outlet for example. In this way, the rechargeable battery 102 for operation can be charged by a simple method.

An example of a portable radiographic apparatus system 120 relating to a third exemplary embodiment of the present invention is described next in accordance with FIG. 10 and FIG. 11. Note that members that are the same as in the first exemplary embodiment are denoted by the same reference numerals, and description thereof is omitted.

Figure 10:
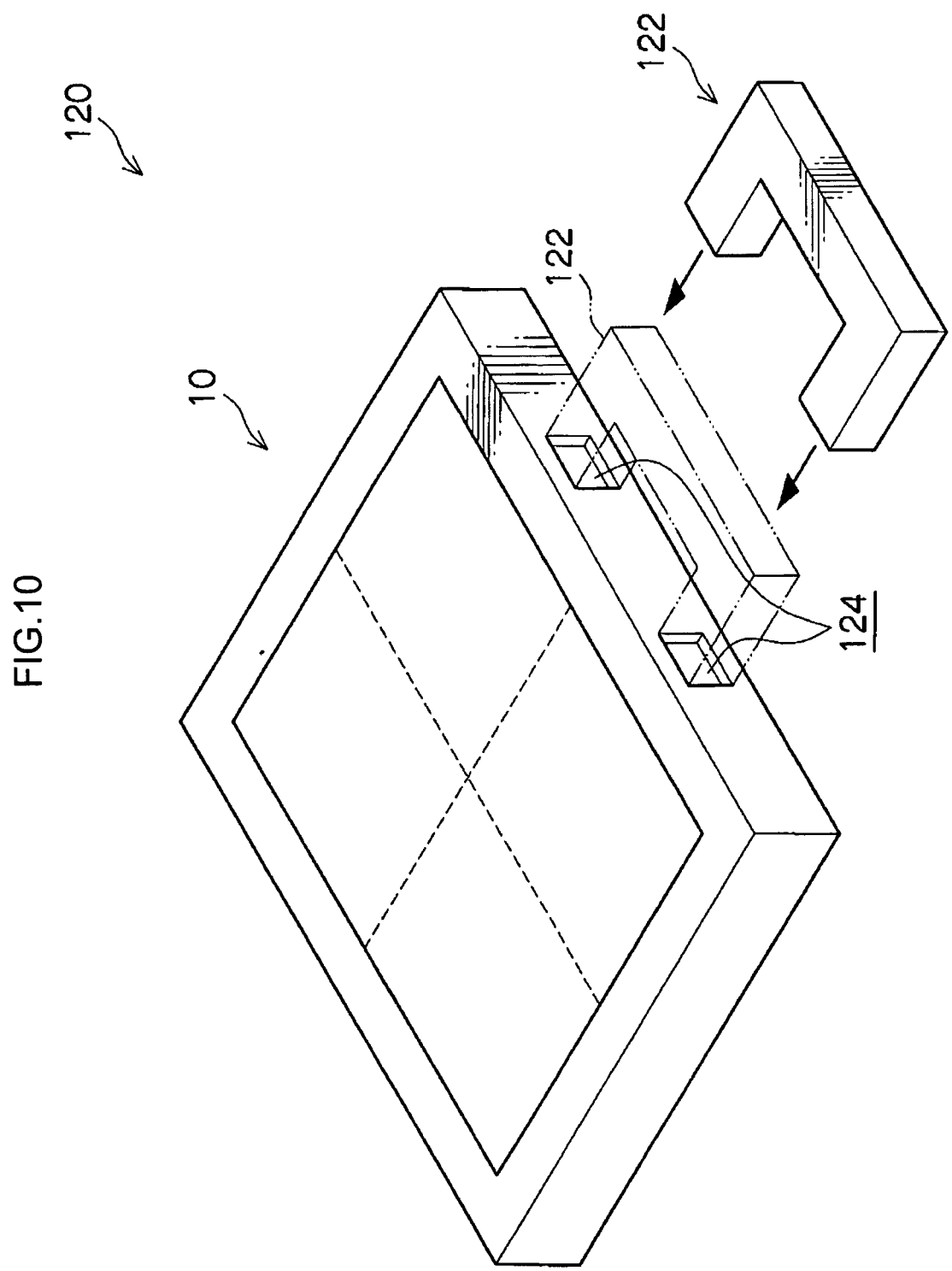
FIG. 10 is a perspective view showing a portable radiographic apparatus that is provided at a portable radiographic apparatus system relating to a third exemplary embodiment of the present invention.

As shown in FIG. 10, differently than in the first exemplary embodiment, a rechargeable battery 122 for operation that is attached to the portable radiographic apparatus 10 is formed in a substantial U-shape. First attachment portions 124, to which the rechargeable battery 122 for operation is attached, are provided in a side surface of the portable radiographic apparatus 10.

When the rechargeable battery 122 for operation is attached to the first attachment portions 124, an unillustrated locking mechanism is operated, and the rechargeable battery 122 for operation is fixed to the first attachment portions 124. In this state, the rechargeable battery 122 for operation can be grasped, and the portable radiographic apparatus 10 can be carried by the rechargeable battery 122 for operation being grasped. Note that, when the rechargeable battery 122 for operation is to be removed from the first attachment portions 124, by operating an unillustrated releasing mechanism, the rechargeable battery 122 for operation can be removed from the first attachment portions 124.

Further, as shown in FIG. 11, a handle portion such as that of the first exemplary embodiment is not provided at the portable X-ray source 70. Two rechargeable batteries 130 for operation, that are attached to the portable X-ray source 70, are formed in substantial U-shapes, in the same way as the rechargeable battery 122 for operation (see FIG. 10). Second attachment portions 132, to which the rechargeable batteries 130 for operation are attached, are provided in the top surface of the portable X-ray source 70.

Moreover, when the rechargeable batteries 130 for operation are attached to the second attachment portions 132, unillustrated locking mechanisms are operated, and the rechargeable batteries 130 for operation are fixed to the second attachment portions 132. In this state, the rechargeable batteries 130 for operation can be grasped, and the portable X-ray source 70 can be carried by the rechargeable batteries 130 for operation being grasped. Note that, when the rechargeable batteries 130 for operation are to be removed from the second attachment portions 132, by operating unillustrated releasing mechanisms, the rechargeable batteries 130 for operation can be removed from the second attachment portions 132.

As described above, the portable radiographic apparatus 10 and the portable X-ray source 70 can be carried by grasping the rechargeable battery 122 for operation and the rechargeable batteries 130 for operation.

What is claimed is:

1. A portable radiographic apparatus system comprising:
    a portable radiographic apparatus that is operated by electric power supplied thereto from a first rechargeable battery, and that records radiographic images expressed by irradiated radiation; and
    a portable X-ray source that is operated by electric power supplied thereto from a second rechargeable battery that has a same shape and same characteristics as the first rechargeable battery, and that irradiates radiation toward the portable radiographic apparatus.

2. The portable radiographic apparatus system of claim 1, wherein
    a first attachment portion, to which the first rechargeable battery is attached so as to be freely attachable thereto and detachable therefrom, is provided at the portable radiographic apparatus,
    a second attachment portion, to which the second rechargeable battery is attached so as to be freely attachable thereto and detachable therefrom, is provided at the portable X-ray source, and
    a total number of the first attachment portions and a total number of the second attachment portions is determined on the basis of consumed electric power of the portable radiographic apparatus and the portable X-ray source per unit number of images at a time of recording radiographic images.

3. The portable radiographic apparatus system of claim 2, wherein, in a state of being attached to the first attachment portion and the second attachment portion, the first rechargeable battery and the second rechargeable battery function as handles of the portable radiographic apparatus and the portable X-ray source, respectively.

4. The portable radiographic apparatus system of claim 1, wherein, in a state of being attached to the portable radiographic apparatus and the portable X-ray source, the first rechargeable battery and the second rechargeable battery function as handles of the portable radiographic apparatus and the portable X-ray source, respectively.

5. The portable radiographic apparatus system of claim 1, wherein an accommodating unit is provided that accommodates at least one of the first rechargeable battery or the second rechargeable battery, and that has an electric cable that supplies electric power from the first rechargeable battery or the second rechargeable battery to the portable radiographic apparatus or the portable X-ray source.

6. The portable radiographic apparatus system of claim 5, wherein a charging cable, that can charge the first rechargeable battery or the second rechargeable battery accommodated in the accommodating unit with electric power from an exterior, is provided at the accommodating unit.

* * * * *